(12) United States Patent
Feinstein

(10) Patent No.: US 10,456,573 B1
(45) Date of Patent: Oct. 29, 2019

(54) MEDICAL CUFF EMPLOYING ELECTRICAL STIMULATION TO CONTROL BLOOD FLOW

(71) Applicant: Feinstein Patents, LLC, Wilkes-Barre, PA (US)

(72) Inventor: Peter A. Feinstein, Palm Beach Gardens, FL (US)

(73) Assignee: Feinstein Patents, LLC, Wilkes-Barre, PA (US)

( * ) Notice: Subject to any disclaimer, the term of this patent is extended or adjusted under 35 U.S.C. 154(b) by 0 days.

(21) Appl. No.: 16/010,721

(22) Filed: Jun. 18, 2018

(51) Int. Cl.
*A61N 1/04* (2006.01)
*A61N 1/36* (2006.01)

(52) U.S. Cl.
CPC ....... *A61N 1/0456* (2013.01); *A61N 1/36014* (2013.01); *A61N 1/36031* (2017.08)

(58) Field of Classification Search
CPC ................. A61N 1/0452; A61N 1/0456; A61N 1/36031; A61N 1/36014
See application file for complete search history.

(56) References Cited

U.S. PATENT DOCUMENTS

| 5,817,138 | A  | 10/1998 | Suzuki |
| 5,974,342 | A  | 10/1999 | Petrofsky |
| 6,826,429 | B2 | 11/2004 | Johnson et al. |
| 7,647,114 | B2 | 1/2010  | Libbus |
| 9,956,405 | B2 | 5/2018  | Goldwasser et al. |
| 2002/0077689 | A1* | 6/2002 | Kirkland ............. A61N 1/0452 607/149 |
| 2004/0118166 | A1* | 6/2004 | Huang ................. A61N 1/0408 66/202 |

(Continued)

FOREIGN PATENT DOCUMENTS

| EP | 0830875 A2 | 3/1998 |
| KR | 20090011617 U | 11/2009 |

(Continued)

OTHER PUBLICATIONS

Hee-Kyung Jin, et al, "Effect of Electrical Stimulation on Blood Flow Velocity and Vessel Size", published online Mar. 6, 2017, https://www.ncbi.nlm.nih.gov/pmc/articles/PMC5385976/.

(Continued)

*Primary Examiner* — Paula J Stice
(74) *Attorney, Agent, or Firm* — Forge IP, PLLC

(57) ABSTRACT

A device covering for controlling blood flow includes a cuff configured to be mounted to an extremity of a patient. The cuff includes a plurality of electrodes electrically connectible to a stimulation power supply. Upon receipt of power from the stimulation power supply, the electrodes supply electrical impulses to the anatomical site in order to stem or stop blood flow. In some cases, the stimulation power supply is an interferential therapy power supply, and a pair of electrodes supplies electrical impulses at two different frequencies, the electrical impulses provided at two different frequencies giving rise to at least one beat impulse having an interference frequency. The beat impulse activates the sympathetic nerves to induce vasoconstriction in the local blood vessels. Alternatively, the beat impulse can be programmed to target the parasympathetic nerves if vasodilatation is desired.

19 Claims, 9 Drawing Sheets

(56) References Cited

U.S. PATENT DOCUMENTS

| | | | |
|---|---|---|---|
| 2006/0041285 A1* | 2/2006 | Johnson | A61N 1/36021 607/46 |
| 2007/0203416 A1* | 8/2007 | Lowe | A61B 5/02208 600/485 |
| 2007/0293917 A1* | 12/2007 | Thompson | A61N 1/0456 607/72 |
| 2010/0131025 A1* | 5/2010 | Henry | A61N 1/0452 607/3 |
| 2010/0268300 A1 | 10/2010 | Ramos Leal et al. | |
| 2011/0288602 A1* | 11/2011 | Nachum | A61N 1/36003 607/3 |
| 2013/0030277 A1* | 1/2013 | Fahey | A61B 5/0492 600/384 |
| 2014/0194949 A1 | 7/2014 | Wichner | |

FOREIGN PATENT DOCUMENTS

| | | |
|---|---|---|
| KR | 20140143938 A | 12/2014 |
| WO | WO2018046570 | 3/2018 |

OTHER PUBLICATIONS

Francisco V. Santos, et al, "Interferential electrical stimulation improves peripheral vasodilatation in healthy individuals", Brazilian Journal of Physical Therapy, vol. 17 No. 3 São Carlos May/Jun. 2013; http://dx.doi.org/10.1590/S1413-35552012005000092.

Akram Shahrokhi, et al, "Impact of interferential current on recovery of pressure ulcers grade 1 and 2", Iranian Journal of Nursing and Midwifery Research, Feb. 2014; 19(7 Suppl1): S91-S96, https://www.ncbi.nlm.nih.gov/pmc/articles/PMC4402989/.

* cited by examiner

MEDICAL CUFF EMPLOYING ELECTRICAL STIMULATION TO CONTROL BLOOD FLOW

FIELD OF THE INVENTION

The invention relates to system employing the use of an electrical stimulator, such as an Interferential Current (IFC) device, or other type of deep penetration electrical stimulation that is non-invasive and external (i.e., transcutaneous), for controlling blood flow. More specifically, the invention relates to a medical cuff, such as a tourniquet, incorporating a mechanism for the delivery of electrical stimulation to the sympathetic/parasympathetic nerves of a relevant extremity to slow or stop bleeding, or to increase blood flow, depending on the medical need.

BACKGROUND OF THE INVENTION

There are a variety of different types of situations in which it is desirable to control a blood flow for therapeutic or surgical reasons. In some cases, it is important to slow or stop the flow of blood in a patient, while in other instances, it is desirable to increase the flow of blood to a particular part of a patient's anatomy.

One example is to stem bleeding. Bleeding is an unavoidable and ever-present consideration in any medical condition or intervention that involves a skin incision (or skin laceration) or procedure directed to deeper/internal organ structures. It is particularly important when performing surgery. This can be especially critical in those cases where the procedure or medical situation has potential to lead to unexpected hemorrhaging. Bleeding, whether minor or major, always presents several challenges.

Undesirable flow of blood in the operative site or operative field must be managed to preserve unobstructed view of anatomic structures to be incised or repaired to avoid surgical errors. This typically necessitates the involvement of an assistant, who will sponge or suction the blood as it accumulates and obscures the local anatomy. This requires an additional set of hands in the operative site, which both results in crowding of the area in which the surgeon needs to work and increases the risk of infection and accidental injury.

Additionally, some medical practitioners have used drapes that contain a pouch to collect the blood (as well as other fluids). For example, during abdominal surgery, a fluid collection pouch may be placed adjacent one side of the surgical site and extending down the side of the patient, while in arthroscopy surgery, the patient's leg may be placed through a collection pouch mounted to a drape, with one sheet of the collection pouch in front of the surgical site on the limb and another sheet of the collection pouch in back of the surgical site, such that the fluid collection pouch is supported in part by the limb itself and in part by the surgical drape (to which the fluid collection pouch is attached). Some drapes include fluid collection pouches with a port for connecting a suction hose to help facilitate removal of the fluid. However, collection pouches pose numerous difficulties, including that the positioning of the pouch can make it difficult to adequately expose the surgical site, that it may not provide an optimal opening for capturing the blood, and that it may leak.

More importantly, intraoperative attempts to stem or stop the blood flow, and the need to arrest post-operative bleeding, have traditionally required the use of additional instruments and/or agents. In particular, pneumatic tourniquets are often employed for this purpose. This consists of using an inflatable cuff to provide tissue compression to occlude the blood flow. The use of such devices suffers from a number of disadvantages.

First, the use of a pneumatic tourniquet to stop intraoperative bleeding is not always effective. Often, bleeding will still occur due to an under-pressurized cuff, insufficient exsanguination, improper cuff selection, a loosely applied cuff, calcified blood vessels resistant to the cuff, or insufficiently quick inflation/deflation.

Additionally, the use of traditional tourniquets to control bleeding at the surgical site has been shown to increase morbidity. A common problem is nerve injury, which appears to be attributable to both mechanical compression and neural ischemia, and which can result in mild transient loss of function to irreversible damage and paralysis. Other potential complications from the use of traditional tourniquets are compartment syndrome, pressure sores, chemical burns, digital necrosis, deep venous thrombosis leading to pulmonary or venous embolization, pain, thermal damage to tissues, and rhabdomyolysis. A common post-operative complication from use of pneumatic tourniquets is hematoma or hemarthrosis formation, from the tourniquet pressure during surgery being too low and allowing arterial blood pressure to push blood from the arterial system past the tourniquet into the extremity while the tourniquet provides enough pressure to prevent the venous blood flow system from returning the blood. The venous blood ends up pooling in the operative site, compromising the surgical field of view, or in the surrounding tissues resulting in a postoperative hematoma, with its many associated complications and difficulties. Similarly, when the tourniquet is deflated after the procedure there is an immediate post-operative reactive hyperemia or vasodilatation, which predisposes one to bleeding in the operative site after the wound is closed.

Further, in difficult cases, a pneumatic tourniquet is not sufficient to adequately slow blood flow. In these cases, in order to sufficiently control bleeding at the surgical site, it is necessary to withdraw the surgical instrument and insert an electrocautery probe through the same opening. To utilize electrocautery, the body of the patient is grounded, and the tip of the energized electrocautery probe is pressed against the tissue from which the blood is flowing. A high frequency electrical current flows from the probe through the tissue of the patient, and the tissue, including any open blood vessels therein, is heated by the current, coagulating the tissue and sealing the open ends of the blood vessels. The blood produced prior to this must then be removed from the surgical site using a flow of sterile fluid (irrigation) to restore visibility in the surgical site, and then the surgical tool is reinserted to resume the surgery.

This removal of the surgical instrument when bleeding occurs, the subsequent insertion of the electrocautery probe, the removal of the probe after cauterization, and the reinsertion of the surgical instrument thereafter is a difficult, time-consuming task that only further increases risk of injury or infection. Moreover, during the time between the removal of the surgical instrument and the insertion of the electrocautery probe, a significant amount of blood can accumulate at the surgical site, making it difficult to visually locate the actual source of the bleeding. Even if one were able to use a single surgical instrument that was also able to act as an electrocautery probe, the cauterization process inflicts undesirable trauma to the relevant tissue.

Efforts to control bleeding often also include the use of pharmaceutical agents. For example, in the past, it was customary to take a unit of the patient's own blood three weeks before the surgery (to allow the body to replenish), which would then be an extra unit of blood to be used during the surgical and post-operative periods, as a method to avoid the complications of HIV and Hepatitis from regular typed and crossed transfusions from the general blood bank. However, this approach still had problems, as it often resulted in a lower starting blood count (patients didn't regenerate to normal levels before the surgery in a three-week time frame). It also did nothing to control the actual problem of bleeding. Currently, transfusions, and the complications associated with them, are rarer because of the use of tranexamic acid, which is sometimes administered (both before and after surgery) to slow the breakdown of blood clots, and thereby prevent blood loss, thus reducing the need for blood transfusions. The side effects of tranexamic acid in the postoperative period can include nausea, constipation, and sensitivity reactions and, although not definitively proven, could potentially be associated with abnormal increased clotting that although it may stop the blood flow, could result in DVT (deep vein thrombosis) and/or pulmonary embolism.

Additionally, pharmacological agents such as bupivacaine and other local anesthetics are sometimes administered preoperatively (as in nerve blocks for regional anesthesia) or to treat post-operative and recovery pain. To help extend the time that these agents are effective, they are often combined with epinephrine. Epinephrine causes vasoconstriction so that the body takes longer to remove the local anesthetic from the area being treated. However, epinephrine has multiple other actions, such as causing tachycardia or elevated blood pressure, that are detrimental to recovery and can cause serious intraoperative and postoperative complications. Such use of epinephrine in this manner needs to be monitored (vital signs) to be sure complications are not occurring. Because these agents or combinations of them can have undesirable side effects, it is preferable to employ a method of controlling intraoperative and post-operative bleeding that does not rely on them.

In other cases, it is desirable to increase (rather than decrease) blood flood to a particular area. For example, after a surgery has been completed and the relevant anatomy sutured back together, it may at some point become beneficial to increase blood flow to the affected area in order to promote healing.

There are various other scenarios in which an increase in blood flow to a specific part of a patient's anatomy can achieve beneficial therapeutic effects. For example, it may be desirable to increase the flow of blood to a patient's foot when treating peripheral vascular disease or after the debridement of diabetic foot ulcers.

Therefore, what is desired is a system and method for controlling blood flow at a surgical site or other wound that does not require having to clear and remove large, or small but strategically localized, amounts of blood exuded by the incision or wound. What is also desired is a system and method for preventing blood loss that does not require the use of excessive pressure that causes trauma to the body. What is further desired is a system and method for preventing blood loss that does not require the use of additional devices that cause other trauma to the body. What is also desired is a system and method for preventing blood loss that does not depend upon the administration of pharmaceuticals. What is further desired is a system and method for controlling blood flow that can increase blood flow to a part of the anatomy, if needed.

SUMMARY OF THE INVENTION

Accordingly, one object of the present invention to provide a system that is able to stop (or at least slow), the bleeding during surgery or resulting from an injury, thereby eliminating (or at least mitigating) the need to manage excessive fluid flow.

It is another object of the present invention to provide such a system for slowing or stopping bleeding that does not require the use of a pneumatic tourniquet.

It is also an object of the present invention to provide such a system for slowing or stopping bleeding that does not require the use of an electrocautery device.

It is yet another object of the present invention to provide such a system that does not require pharmacological effects in order to slow or stop the bleeding.

It is still another object of the invention to provide a system that, if needed, stimulates blood flow and vasodilatation if that is a condition deemed to be needed for the particular procedure being undertaken.

In order to overcome the deficiencies of the prior art and to achieve at least some of the objects and advantages listed, one exemplary embodiment of the invention comprises a device for controlling blood flow, including a cuff configured to mount to the extremity of a patient, where the cuff includes a plurality of electrodes electrically connectable to a stimulation power supply, and where the electrodes supply electrical impulses to the extremity of the patient when receiving power from the stimulation power supply.

In some advantageous embodiments, the stimulation power supply comprises an interferential therapy power supply, and the plurality of electrodes comprises at least one pair of electrodes supplying electrical impulses at two different frequencies, the electrical impulses provided at two different frequencies giving rise to at least one beat impulse having an interference frequency.

In some of these embodiments, the at least one beat impulse has a sympathetic nerve stimulation property to induce vasoconstriction of blood vessels. In some embodiments, the at least one beat impulse has a parasympathetic nerve stimulation property to induce vasodilatation of blood vessels.

In certain advantageous embodiments, the cuff comprises an inflatable cuff. In some cases, the invention further includes a fluid source that supplies fluid to the inflatable cuff to provide pneumatic pressure. In these embodiments, the IFC can be used in conjunction with pneumatic pressure, as described in further detail below.

In some advantageous embodiments, the cuff includes a plurality of pairs of electrodes, each pair giving rise to at least one beat impulse having an interference frequency.

In some embodiments, the electrodes are embedded within the cuff. In other embodiments, each electrode includes an adhesive on a surface thereof, with which the electrode is affixed to an outer surface of the cuff. In still other embodiments, the cuff includes a plurality of enclosed chambers, each of the chambers having an electrically conductive liquid therein, and the electrodes comprise the electrically conductive liquid. In still other embodiments, the cuff includes a plurality of electrically conductive fabric segments of fabric, and the electrodes comprise the electrically conductive fabric segments.

In certain advantageous embodiments, the invention further includes a controller, a stimulation power supply in communication with the controller, and a sensor providing sensor feedback to the controller, the sensor indicative of the state of blood flow at the extremity, where the controller causes the stimulation power supply to supply power to the plurality of electrodes based at least in part on the state of blood flow.

In some of these embodiments, the sensor comprises a targeting or monitoring device. In some cases, the sensor comprises a Doppler ultrasound probe.

In certain embodiments, each electrode includes an electrical connector for connecting a wire to the stimulation power supply. In some embodiments, the stimulation power supply communicates wirelessly with the electrodes.

The invention also comprises a device covering for controlling blood flow, including an interferential therapy power supply, a cuff configured to mount to the extremity of a patient, the cuff including at least one pair of electrodes connected to the interferential therapy power supply, where the pair of electrodes supplies electrical impulses at two different frequencies when receiving power from the interferential therapy power supply, the electrical impulses provided at two different frequencies giving rise to at least one beat impulse having an interference frequency The invention also comprises a method of controlling blood flow, including mounting a cuff to the extremity of a patient, the cuff having a plurality of electrodes, connecting the plurality of electrodes to a stimulation power supply, and supplying electrical impulses to the extremity by supplying power to the electrodes from the stimulation power supply.

In some of these embodiments, the stimulation power supply comprises an interferential therapy power supply, and the step of supplying electrical impulses to the extremity comprises supplying electrical impulses at two different frequencies, the electrical impulses provided at two different frequencies giving rise to at least one beat impulse having an interference frequency.

In some of these embodiments, the step of mounting a cuff to the extremity of a patient comprises mounting the cuff to the patient's ankle. In other embodiments, the step of mounting a cuff to the extremity of a patient comprises mounting the cuff to the patient's wrist. In other embodiments, the step of mounting a cuff to the extremity of a patient comprises mounting the cuff to the patient's thigh.

DETAILED DESCRIPTION OF THE INVENTION

As used herein, the terms "electrode" and electrodes" encompass electrical coils, electrical plates, electrical conductors, conductive fabrics and gels, and any other conductive materials and devices.

Figure 1:
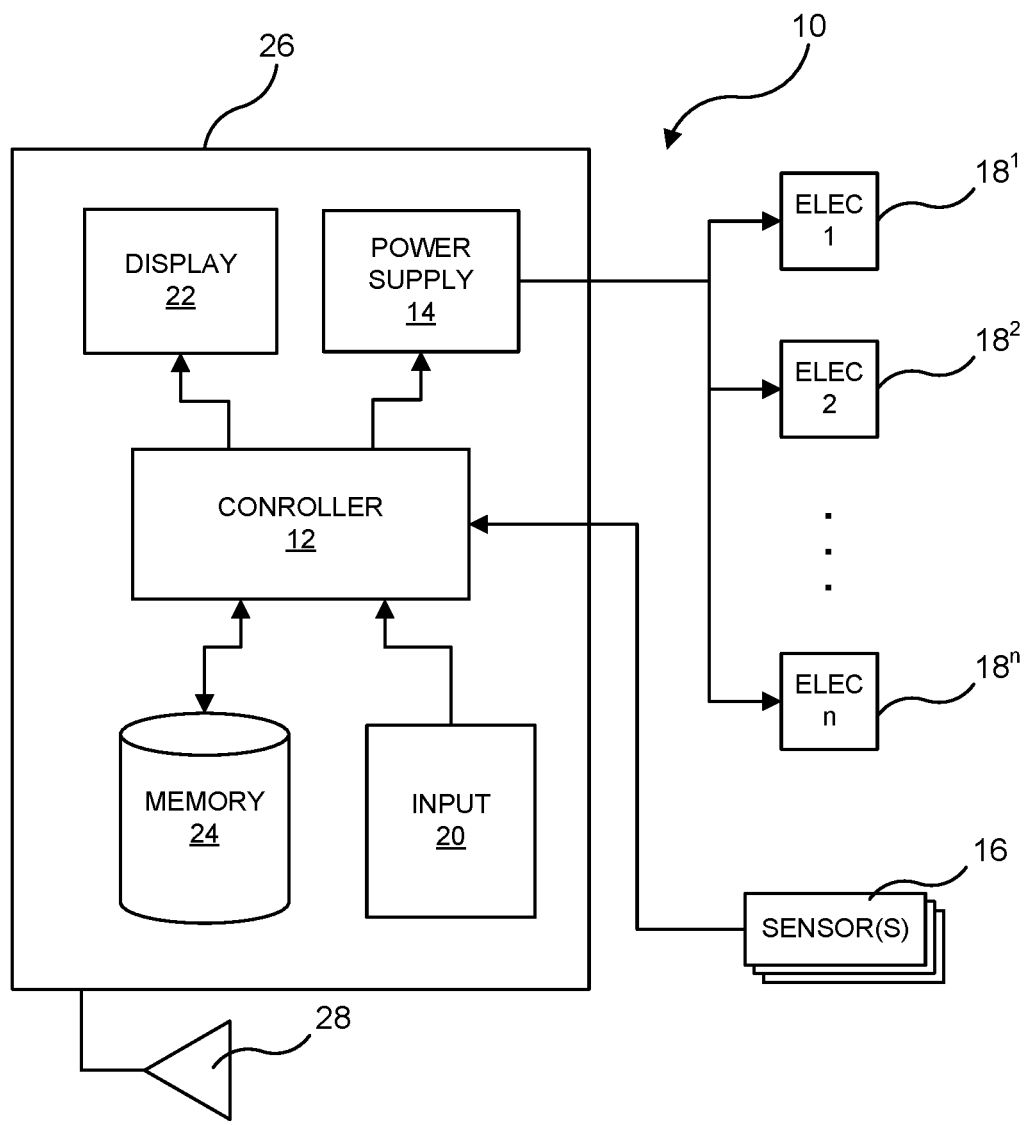
FIG. 1 is a block diagram illustrating a system for controlling blood flow with a cuff in accordance with an exemplary embodiment of the present invention.

Referring to the figures in detail and first to FIG. 1, there is shown an exemplary embodiment of a system (10) for controlling blood flow in a surgery patient or other individual requiring the active control and/or prevention of blood flow. The system (10) includes a controller (12) and a stimulation power supply (14) in communication with the controller (12).

The system (10) also includes a plurality of electrodes ($18^1$, $18^2$ . . . $18^n$) in electrical communication with the stimulation power supply (14). The plurality of electrodes ($18^1$, $18^2$ . . . $18^n$), the location of which are described further below, are arranged to supply electrical impulses that cause activation of sympathetic and/or parasympathetic nerves when supplied power by the stimulation power supply.

The controller (12) causes the stimulation power supply (14) to supply power to the plurality of electrodes ($18^1$, $18^2$ . . . $18^n$) in response to a command from the controller (12) when the stemming or arresting of bleeding is required. As is explained in more detail below, the power supplied to the plurality of electrodes ($18^1$, $18^2$ . . . $18^n$) is such that transcutaneous electrical impulses are created in order to cause sympathetic and/or parasympathetic nerve activation.

The system (10) also includes an input mechanism (20), such as a graphical user interface, microphone for receiving voice commands, keyboard, joystick, or the like, which allows the user to enter control parameters and the like. As examples, input mechanism (20) may include a button or other type of controller to turn the device on or off manually, or to trigger activation of sympathetic and/or parasympathetic nerves.

In some embodiments, the system also includes a sensor (16) providing sensor feedback to the controller (12), and the controller (12) causes the stimulation power supply (14) to supply power to the plurality of electrodes ($18^1$, $18^2$ . . . $18^n$) based, at least in part, on the sensor feedback received from the sensor (16). For instance, the sensor feedback may be indicative of the blood flow rate through a relevant circulatory path of the patient, such that a medical practitioner can monitor blood flow as the electrical stimulus is being applied. The sensor (16) may comprise, for example, an ultrasound probe. In this sense, a Doppler ultrasound can be used to generate an image of the movement of blood and its velocity relative to the probe in the target area. This may be particularly desirable, for example, when direct visualization of subdermal/internal bleeding is impractical, or when the system is being used post-operatively and one is unable to directly observe whether there is any post-operative bleeding.

In some embodiments, the system (10) also includes a display (22) to provide visual and/or auditory output to a user of the system (10). The display (22) may also present the user with other helpful information, such as previously loaded data for the patient, or current blood flow and previously recorded blood flow rates for the targeted circulatory pathways prior to the supply of power to the electrodes ($18^1$, $18^2$ . . . $18^n$) such that a medical practitioner can perform a comparison to determine whether the electrical stimulus is actively affecting the targeted pathway.

The system (10) further includes a memory (24), which allows the system to store various parameters that may be employed by the controller (12), or data recorded prior to and/or during the supply of power to the electrodes ($18^1$, $18^2$ . . . $18^n$).

In some embodiments the system further includes the ability to transmit information and data obtained through the Internet or other mechanism to remote or off site locations for consultation or expert input, interpretation, and monitoring of data garnered during or after the procedure, or for incorporation into EMRs, or for telehealth applications.

The controller (12), stimulation power supply (14), input mechanism (20), display (22), memory (24) and an optional antenna (28) for wireless communication may be (but are not necessarily) contained in a housing (26), as should be apparent to those skilled in the art. Various types of connectors may be provided on the housing to allow for connection of the electrodes ($18^1$, $18^2$ ... $18^n$), the sensor (16), or various other devices (e.g., mobile phones, tablets, smart watches, etc.), as should also be apparent to those skilled in the art. This connection may be wired (which requires grounding in a manner similar to that of an electrocoagulation device), or wireless, as further described below.

While specific targeting for the IFC impulses will typically not be required for the present invention, the controller (12) can be connected to a targeting device, if desired. Depending on whether the surgeon, nurse, or other medical practitioner is able to eyeball the appropriate positioning of the tourniquet, or whether a more precise correlation with other surgical instrumentation (such as robotic surgery) or post-operative positioning is required, a targeting system may be employed.

For example, many imaging modalities are known that would be appropriate to collect imaging sensor data, including ultrasound (including Level II ultrasound, 3D ultrasound, 4D ultrasound, etc.), x-rays, computed tomography (CT) scanning, magnetic resonance imaging MRI scanning (3D or otherwise), positron emission tomography (PET), radiography, elastography, thermography, bone scanning, etc. More advanced imaging techniques involving combinations of various modalities may also be used, such as MRI-TRUS (magnetic resonance imaging/transrectal ultrasound) fusion, which has been used to perform targeted prostate biopsies.

The imaging modalities used may be static or dynamic. In addition, various functional modalities may be employed, such as Doppler ultrasound to evaluate blood flow or other forms of plethsmethography (which is measurement of blood flow dynamics). Image intensification is another diagnostic modality that can be used, which affords x-ray assessment in real time with motion as in some of the ultrasound options.

Additionally, various other types of electrical sensor data may be used to assist with targeting of the IFC currents. For example, echocardiography (EKG) nerve conduction tests, electromyograms (NCT and NCV) and somatosensory evoked potentials (SSEP) may also be employed.

The sensor(s) may be integrated with a robotics device, machine, or algorithm. Examples of this would be surgical robotics machines made by MAKO Surgical, Intuitive Surgical, and Restoration Robotics which respectively are used for surgically-assisted operations in terms of joint replacements, robotic abdominal surgery, robotic placement of hair transplant follicles, and robotic assisted prostate surgery. Rather than using robotics to aid surgeons, the robotics technology can be combined with IFC to give extremely accurate microscopic and larger field targeting through the IFC.

In fact, the robotics could be combined with IFC such that an individual could do essentially "IFC robotic surgery" in which the robotic assisted mechanism not only targets the area through robotic anatomic analysis, but also then the robotic arms controlled by the surgeon would place the appropriate interferential electrodes on the skin and, through the connecting robotic arm also supply the appropriate electric current with feedback through the robotic surgery targeting technology and device.

Although the use of various types of deep penetration electrical stimulation that are non-invasive and external (i.e. transcutaneous) is contemplated, the presently discussed exemplary embodiment employs interferential current (IFC) technology.

In general, IFC therapy utilizes two medium frequency currents which pass through the tissues simultaneously. They are set up so that their paths cross; and in simple terms they interfere with each other. This interference gives rise to an interference or beat frequency, which has the characteristics of low-frequency stimulation. The exact frequency of the resultant beat frequency can be controlled by the input frequencies. For example, if one current were at 4000 Hz and the other current at 3900 Hz, the resultant beat frequency would be at 100 Hz.

Thus, the basic principle of IFC therapy is to utilize the strong physiological effects of the low frequency electrical stimulation of muscle and nerve tissues at sufficient depth, without the associated painful and somewhat unpleasant side effects of such stimulation. The medium frequency currents penetrate the tissues with very little resistance, whereas the resulting interference current (low frequency) is in the range that allows effective stimulation of the biological tissues. The resistance (impedance) of the skin is inversely proportional to the frequency of the stimulating current.

In other words, the lower the stimulation frequency, the greater the resistance to the passage of the current, so more discomfort is experienced. The skin impedance at 50 Hz is approximately 3200 ohms, whilst at 4000 Hz, it is reduced to approximately 40 ohms. The result of applying this latter frequency is that it will pass more easily through the skin and any other tissues before hitting the target tissue or organ with a therapeutic beat frequency resulting in the desired physiologic response from the target organ or tissue, requiring less electrical energy input to the deeper tissues, giving rise to less discomfort.

Figure 2:
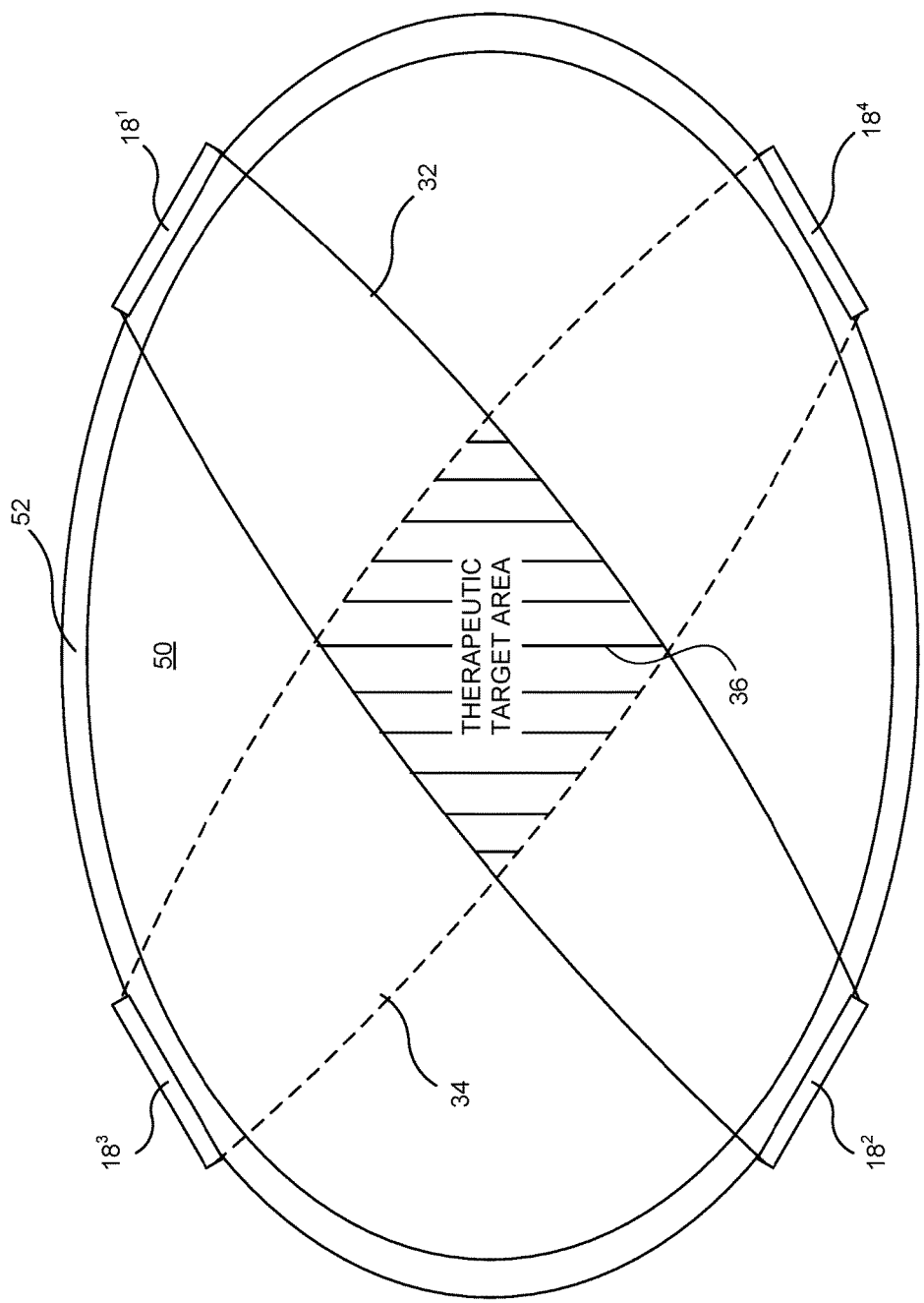
FIG. 2 is schematic view illustrating operational characteristics of the system shown in FIG. 1.

Referring now to FIG. 2, an exemplary arrangement of electrodes employing IFC therapy is shown applied to the epidermis (52) of a patient (50). In this example, a first pair of electrodes ($18^1$, $18^2$) supplies transcutaneous electrical impulses (32) at a first frequency (represented by solid lines) and a second pair of electrodes ($18^3$, $18^4$) supplies transcutaneous electrical impulses (34) at a second frequency (represented by dashed lines) different than the first frequency. The transcutaneous electrical impulses (32, 34) provided at the first and second frequencies giving rise to a beat impulse (36) in a Therapeutic Target Area (located at the position shown in FIG. 2 where the area defined by solid lines and the area defined by dashed lines overlap) having an interference frequency. The beat impulse (36) results in activation of the sympathetic and/or parasympathetic nerves.

The beat impulse is controlled depending on the type of nerve/tissue/organ to be stimulated, as well as on real-time feedback of the elicited response (as explained in more detail below). For example, it has been found that beat impulses having a frequency in the range of from 1-5 Hz may provide desirable stimulation properties for sympathetic nerves, beat impulses having a frequency in the range of from 10-150 Hz may provide desirable stimulation properties for parasympathetic nerves, beat impulses having a frequency in the range of from 10-50 Hz may provide desirable stimulation properties for motor nerves, beat impulses having a frequency in the range of from 90-100 Hz may provide desirable stimulation properties for sensory nerves, beat impulses having a frequency in the range of from 90-150 Hz may provide desirable stimulation properties for nociceptive fibers, and beat impulses having a frequency in the range of from 1-10 Hz may provide desirable stimulation properties for smooth muscle. As will be recognized, other types of nerves/tissues/organs may respond to other beat impulse frequencies.

As has been recognized, nerves will sometimes acclimate to a constant signal. Accordingly, in some embodiments, the electrodes vary the beat frequency, either automatically or upon user input from a medical practitioner, to produce a frequency "sweep" that avoids this problem.

Figure 3:
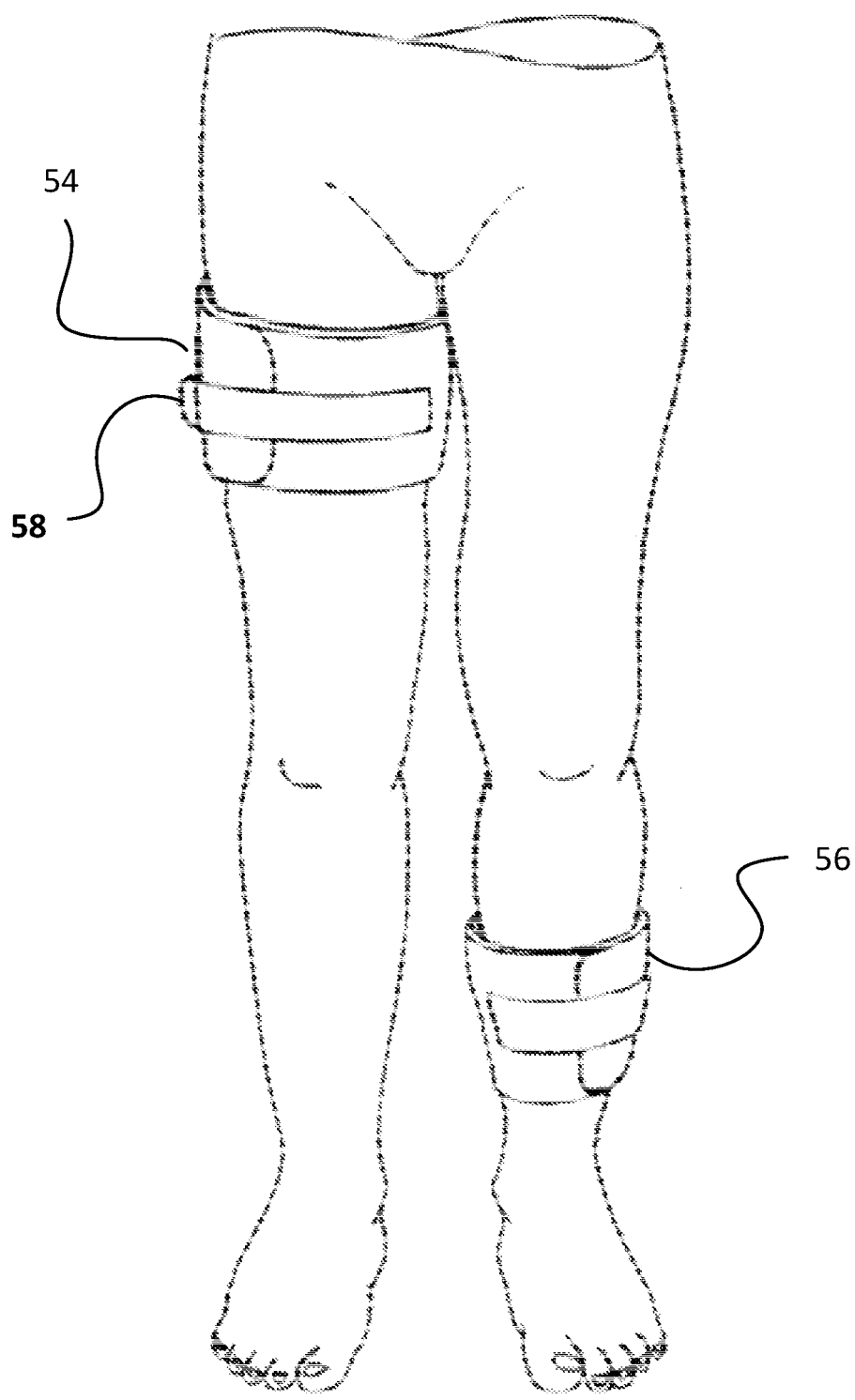
FIG. 3 is a perspective view of the cuff used in the system of FIG. 1 being used on a patient.

Referring now to FIG. 3, an exemplary device for controlling blood flow in accordance with the invention is shown. The device comprises a cuff (54) or (56) configured to be secured to an extremity of a patient. As shown, a cuff (54) could be secured to a patient's thigh when, for example, the patient is undergoing arthroscopic surgery, such that it can be used to stem blood flow to the knee. Similarly, as shown, a cuff (56) could be secured at or above a patient's ankle. This could be for the purpose of decreasing/stopping blood flow, such as may be desirable during a surgical procedure on the foot, for example, or for the purpose of increasing blood flow, such as may be desirable to treat peripheral vascular disease in the foot, for example. As previously noted, different frequencies can be used to stimulate different nerve types, depending on which effect is desired.

The cuff may be wrapped around the patient's extremity and secured thereto according to any conventional means, as is well understood in the art. For instance, the cuff (54) may have a strap and buckle (58), as shown. As another example, and as shown in FIG. 4A, the cuff (60) may have an attachment portion (62) that overlaps with the other end of the cuff, such as a hook and loop fastener, by which the cuff (60) is secured to the extremity.

Figure 4A:
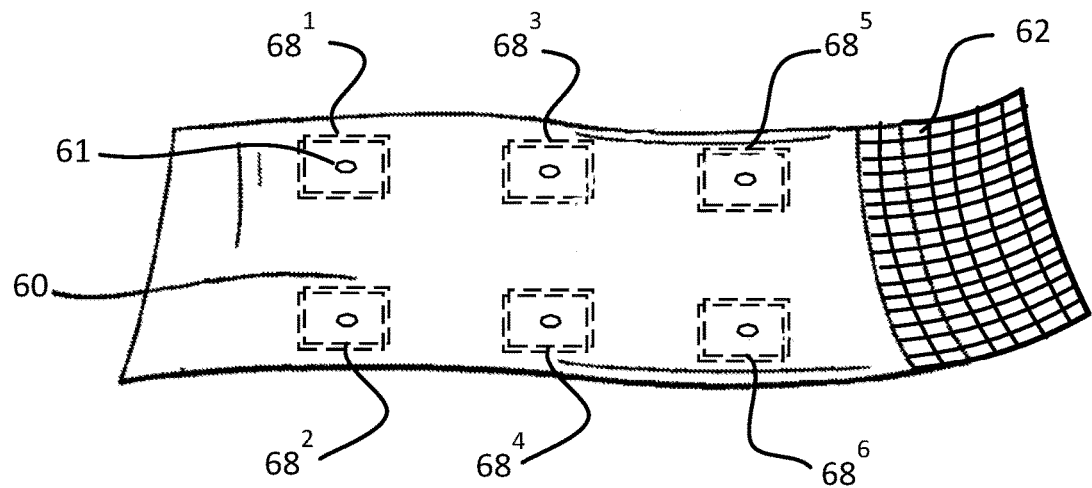
FIGS. 4A-D are perspective views of exemplary cuffs used in the system illustrated in FIG. 1.

Referring now to FIG. 4A, an exemplary cuff (60) is shown. The cuff (60) may be made of a fabric or any other suitable flexible and/or stretchable material. A plurality of electrode pairs $(68^1/68^2)$, $(68^3/68^4)$, $(68^5/68^6)$ are embedded in the material of the cuff for applying the IFC therapy. The electrodes $(68^1/68^2)$, $(68^3/68^4)$, $(68^5/68^6)$ are connected to at least one power supply (14), as previously described. If hardwired to the power supply (14), the wires may be permanently connected to the electrodes $(68^1/68^2)$, $(68^3/68^4)$, $(68^5/68^6)$. Alternatively, once the cuff (60) is mounted to a patient's extremity, the wire ends can be connected to the electrodes via quick connection ports (61) already mounted in the cuff (60) or other customary means of connecting the wires thereto. This is particularly useful in surgical scenarios, where sterile wire ends can be connected once the cuff (60) is properly secured to the patient in the sterile field. The wires are of sufficient length to travel out of the surgical field so that a circulating nurse can connect the other end to the power supply.

Though the connection between the electrodes $(68^1/68^2)$, $(68^3/68^4)$, $(68^5/68^6)$ and power supply (14) can be a hard-wire connection, it is often desirable to minimize the number of wires entering the sterile field. Therefore, in some embodiments, the electrodes include an antenna and are instead wirelessly connected to the power supply, as has been known in connection with the use of existing wireless TENS (Transcutaneous Electrical Nerve Stimulation) units.

The electrodes $(68^1/68^2)$, $(68^3/68^4)$, $(68^5/68^6)$ may comprise pads or other appropriate conductive material, some examples of which are described in further detail below. The electrodes can be of various sizes. The size of the electrode will affect the size of the target therapeutic area, and so generally speaking, the larger the electrodes $(68^1/68^2)$, $(68^3/68^4)$, $(68^5/68^6)$ can be while still reasonably fitting in the particular cuff being employed, the better.

The electrode portions of the cuff (60) include a conductivity backing that, in addition to the adhesive, is directly in contact with the skin. This can be a gel, such as the conductive gel commonly used with an ultrasound probe, or a moist pad, as is commonly used with EKG leads. The electrode portions are already provided with the gel or other conductive material, such that the cuff (60) can be applied to the patient in a simple, sterile step during preparation for surgery.

Figure 4B:
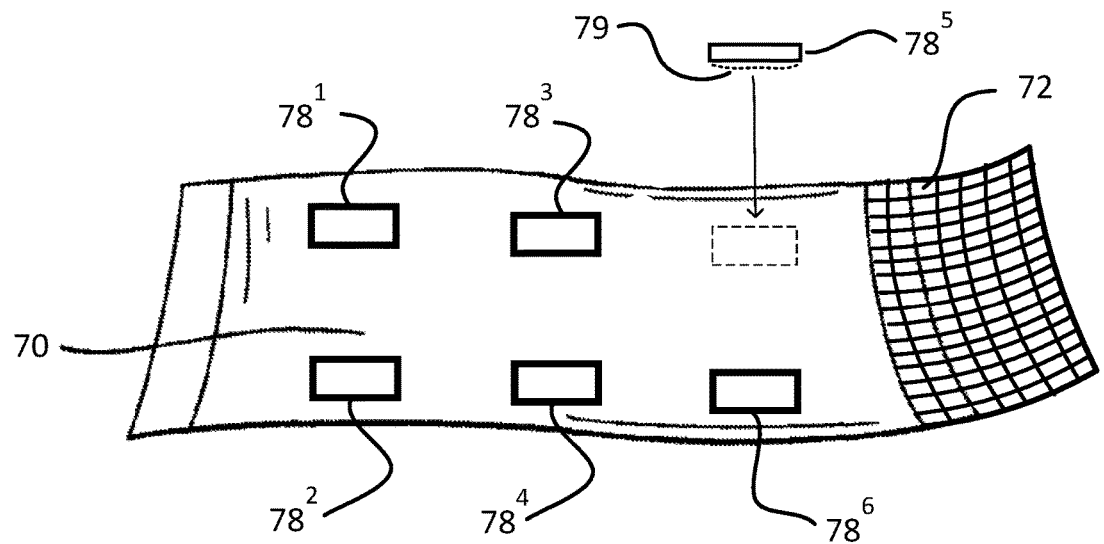

Another exemplary embodiment of a cuff is illustrated in FIG. 4B. In these embodiments, a cuff (70) includes a plurality of electrodes $(78^1/78^2)$, $(78^3/78^4)$, $(78^5/78^6)$ affixed to an outer surface of the drape. In some cases, the electrodes $(78^1/78^2)$, $(78^3/78^4)$, $(78^5/78^6)$ comprise a pad with an adhesive one side, such that the electrodes $(78^1/78^2)$, $(78^3/78^4)$, $(78^5/78^6)$ can be affixed to the cuff (70) after the cuff (70) has applied to the patient, and the wires to the power supply (14) then connected to the electrodes.

Figure 4C:
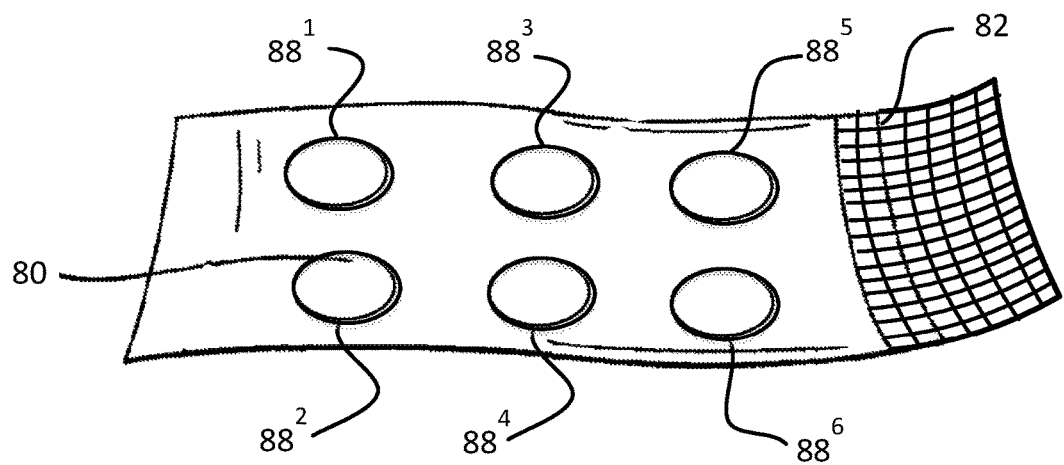

Another exemplary embodiment of a cuff is illustrated in FIG. 4C. In these embodiments, a cuff (80) includes a plurality of enclosed chambers therein. The chambers are filled with an electrically conductive fluid, such that they serve as electrodes $(88^1/88^2)$, $(88^3/78^4)$, $(88^5/88^6)$ for delivering the electrical stimulus.

Figure 4D:
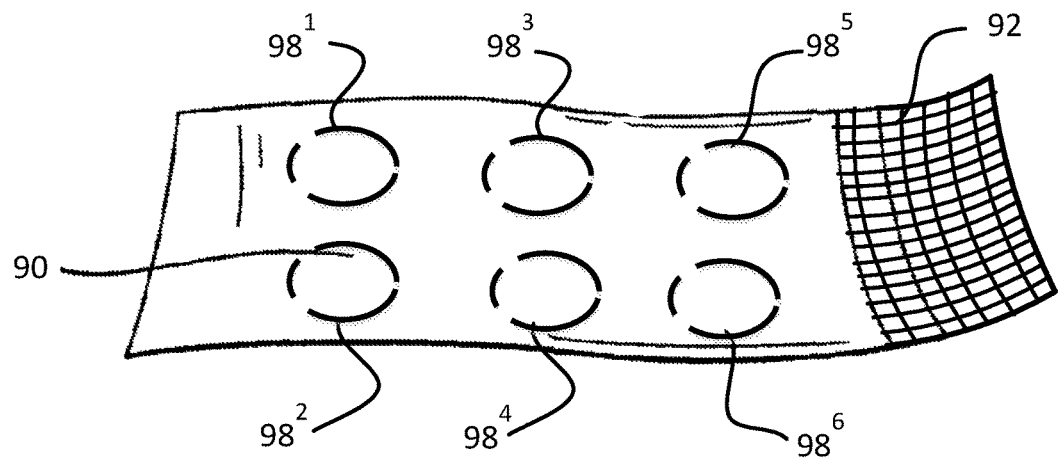

In another exemplary embodiment, the cuff (90) itself is fashioned from both electrically conductive and non-electrically conductive portions. As shown in FIG. 4D, in these embodiments, a plurality of segments of electrically conductive fabric serve as electrodes $(98^1/98^2)$, $(98^3/98^4)$, $(98^5/98^6)$, for delivering the electrical stimulus.

Figure 5A:
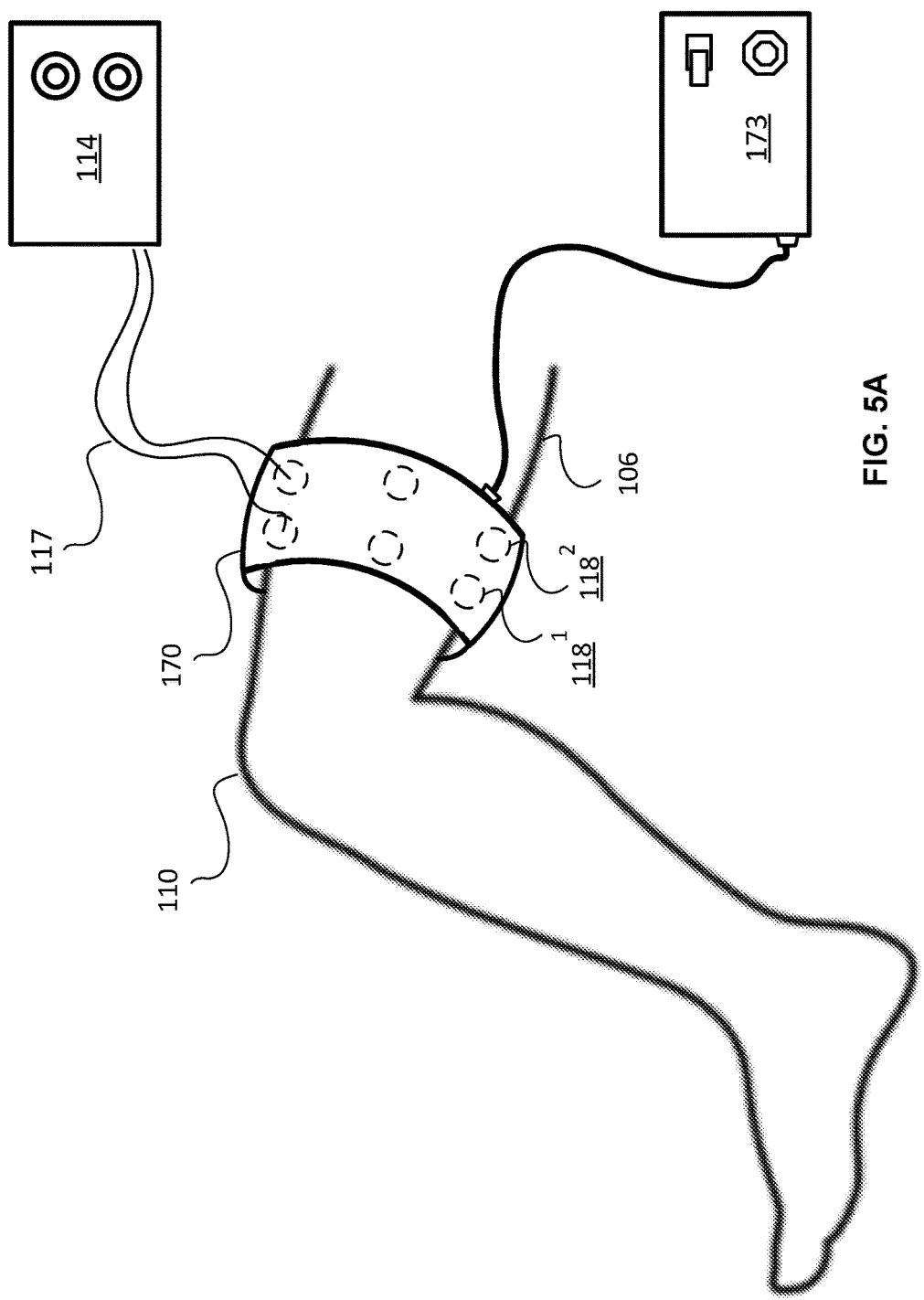
FIGS. 5A-B are partially perspective views of the cuff of FIGS. 4A-D being used on a patient's thigh.
Figure 5B:
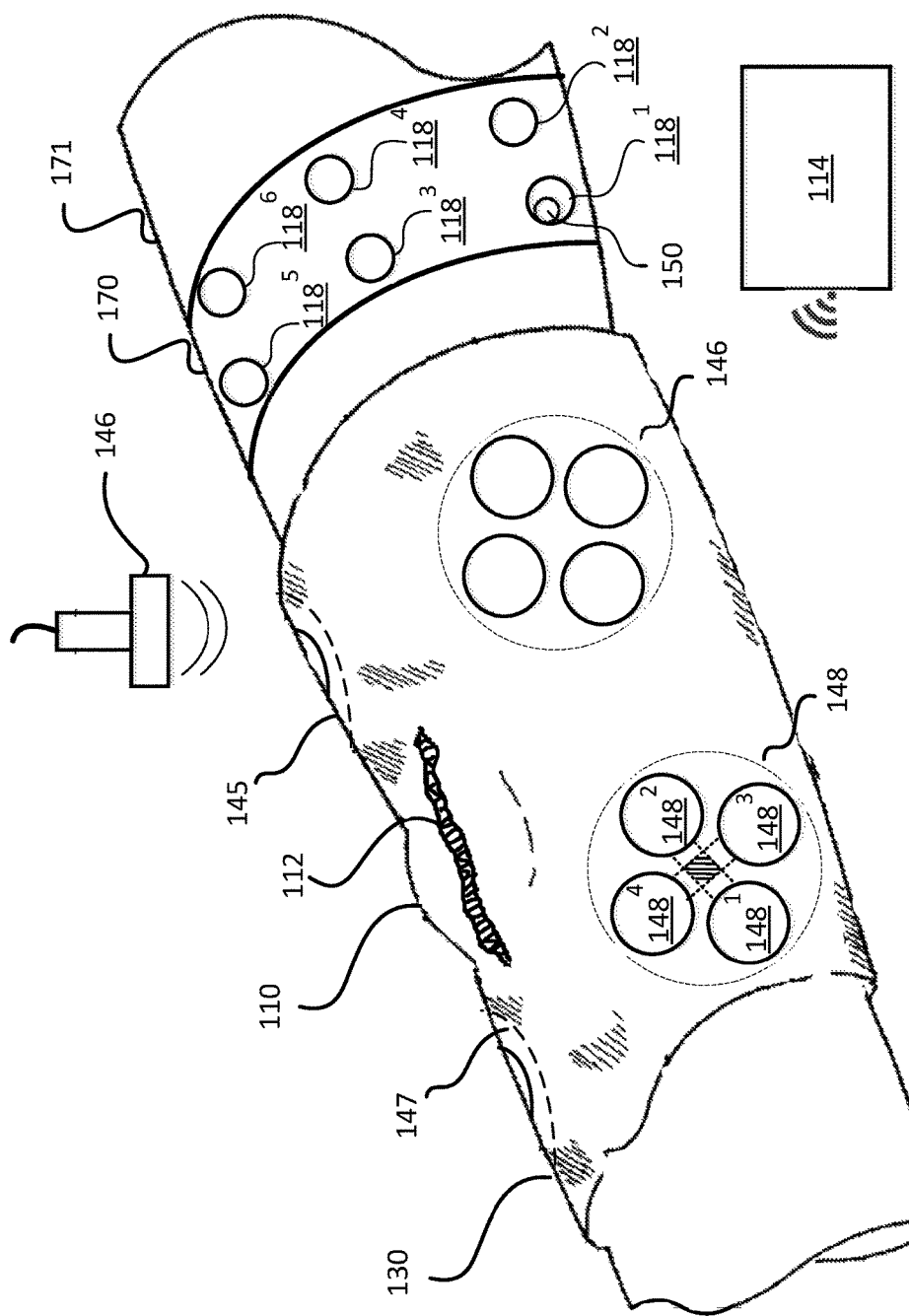

Referring now to FIG. 5A-B, a typical application of the cuff applying IFC therapy is shown. In this example, the cuff functions as a tourniquet in connection with knee surgery.

As shown in FIG. 5A, prior to beginning surgery, a cuff (170) is secured to the thigh (106) of a patient above the knee (110). The cuff (170) has a series of electrode pairs $(118^1/118^2)$, $(118^3/118^4)$, $(118^5/118^6)$, which are connected via wires (117) to the power supply (114). As shown in FIG. 5B, a sterile drape (130) is placed about the knee (110) of the patient, where an incision (112) is made and subsequently sutured together. The drape (130) may also apply IFC therapy, if desired. In these cases, the drape (130) has a series of electrode pairs $(148^1/148^2)$, $(148^3/148^4)$, which are connected via wires, or wirelessly, to the same or different power supply (114).

When bleeding occurs during the surgery, the surgeon or other medical practitioner causes the power supply (114) (e.g., by simply turning it on or by issuing a command via a controller, as described above) to supply power to the electrodes $(118^1/118^2)$, $(118^3/118^4)$, $(118^5/118^6)$. As a result, each electrode pair $(118^1/118^2)$ delivers electrical impulses at two different frequencies, giving rise to at least one beat impulse having an interference frequency.

The electrodes $(118^1/118^2)$ are located such that the therapeutic target area thereof is positioned to cause sympathetic nerve stimulation in order to cause vasoconstriction of blood vessels contributing to the undesirable bleeding. While activation of sympathetic nerves will typically cause vasodilatation relative to organs needed for a "fight or flight" response, sympathetic activation generally constricts blood vessels, thereby increasing vascular resistance and decreasing blood flow. This effect on the blood flow tends to be particularly prominent in relation to the skin, digestive tract, and skeletal muscle. Accordingly, upon receiving power from the power supply, the electrodes activate the sympathetic nerves to induce local constriction of the blood vessels in the targeted area, which operates to reduce, or stop, the flow of blood.

As mentioned previously, when activation of the sympathetic nerves it desirable, beat impulses having a frequency in the range of from 1-5 Hz may provide desirable stimulation properties.

In instances where it is desirable to achieve vasodilatation, the parasympathetic nerves can be targeted. For example, after repair of an incision/laceration and/or during recovery, there comes a time when active bleeding has stopped and, rather than needing to slow/stop blood flow, it may be desirable to induce vasodilatation to instead increase blood flow to the wound that is now trying to heal. At these times, the cuff can be used to facilitate more rapid healing by targeting the parasympathetic nerves. As mentioned previously, when activation of the parasympathetic nerves is desirable, beat impulses having a frequency in the range of from 10-150 Hz may provide desirable stimulation properties.

As with electrode pair ($118^1/118^2$), electrode pairs ($118^3/118^4$), $118^5/118^6$) are likewise positioned such the therapeutic target area thereof is positioned to cause the desired sympathetic or parasympathetic nerve stimulation in order to cause vasoconstriction of the blood vessels that are contributing to the undesirable bleeding. Any number of electrode pairs may be employed on the cuff (170) in this manner.

Optionally, an ultrasound probe (146) or other targeting device/mechanism is used to image the blood flow as described above to help the medical practitioner assess whether particular electrodes at their particular locations are indeed having the intended effect at the relevant target area. Notably, in cases where the electrodes are affixed to the cuff (170) via an adhesive, such as described in reference to FIG. 4B, the electrodes can be removed and repositioned if the desired effect is not being achieved.

In this example, the invention is employed in connection with a total knee arthroplasty (TKA), or total knee replacement (TKR). Blood loss is a serious concern during these procedures, and allogeneic transfusions are commonly used to treat the acute blood loss and postoperative anemia that often occurs, but these transfusions are associated with the risks of allergic and immunologic reactions, and infection transmission. Hence, multiple blood-saving strategies have been employed to try to minimize blood loss, reduce transfusion rates, and decrease complications, for which the present invention is ideally suited.

In this instance, the cuff (170) is secured to the thigh (171) of the patient, proximal to the surgical site (i.e., proximal to the knee 110). The power supply (114) supplies power to the electrode pairs ($118^1/118^2$), ($118^3/118^4$), ($118^5/118^6$), which in turn, deliver the IFC nerve stimulation necessary to cause vasoconstriction of the blood vessels. A self-adhesive drape (130), which can be an IFC drape as noted above, is applied the patient's knee, and an incision (112) is cut through the drape (130) to perform the procedure. The IFC therapy continues to be applied by the cuff (170), and possibly also the drape (130), during the procedure in order to continue to control the blood flow at the thigh. By intercepting the incoming arteries and smaller arterioles in the upper thigh with the cuff (170) in this manner, the medical practitioner is able to stop, or at least slow, the flow of blood proximal to the knee (110), thereby reducing bleeding at the surgical site.

The cuff (170) can also be inflatable and connected to a fluid source (173) for supplying a fluid (typically air) to the cuff (170), as shown in FIG. 5A. As a result, the IFC can be used in conjunction with pneumatic pressure if needed in order to control the blood flow. This is useful in scenarios in which the IFC isn't sufficient to fully control the flow of blood. Pressure can be applied as in the use of traditional pneumatic tourniquets, but it can be applied at reduced pressure, or for reduced time, than would otherwise be required in view of the application of the IFC. A timer with an alarm may be provided, which alerts the surgeon that a certain interval for which the pressure has been applied has expired (e.g., 15 or 30 minutes, so that the surgeon can then deflate (or remove) the cuff (170) to provide a recovery interval (e.g., 10 or 15 minutes) in order to avoid potential complications.

Post-surgery, when active bleeding has stopped, the cuff (170) may be used to instead induce vasodilatation to increase blood flow to the area that is now trying to heal, as described above.

If wireless, each set of electrode pairs ($118^1/118^2$), ($118^3/118^4$), $118^5/118^6$) includes at least one antenna (150) for receiving power wirelessly from the power source (114). Each electrode may have its own antenna, or the electrodes in a localized set of electrodes ($118^1/118^2$), ($118^3/118^4$), $118^5/118^6$) may be wired together, such that only a single electrode ($118^1$) needs to wirelessly receive power from the power supply (114), which it then communicates to the remaining electrodes in the localized set.

A user input of some form, such as on the controller (12) described above, may be provided for the cuff (170) and/or the drape (130) to allow a user to set the Hz level and program the device for either vasoconstriction or vasodilatation, depending on what is desired.

Although the invention has been described in connection with total knee arthroplasty, it can be used in connection with any surgical procedure in which intraoperative or post-operative control of bleeding is needed, including endarterectomies and endovascular and bypass surgeries.

Figure 6:
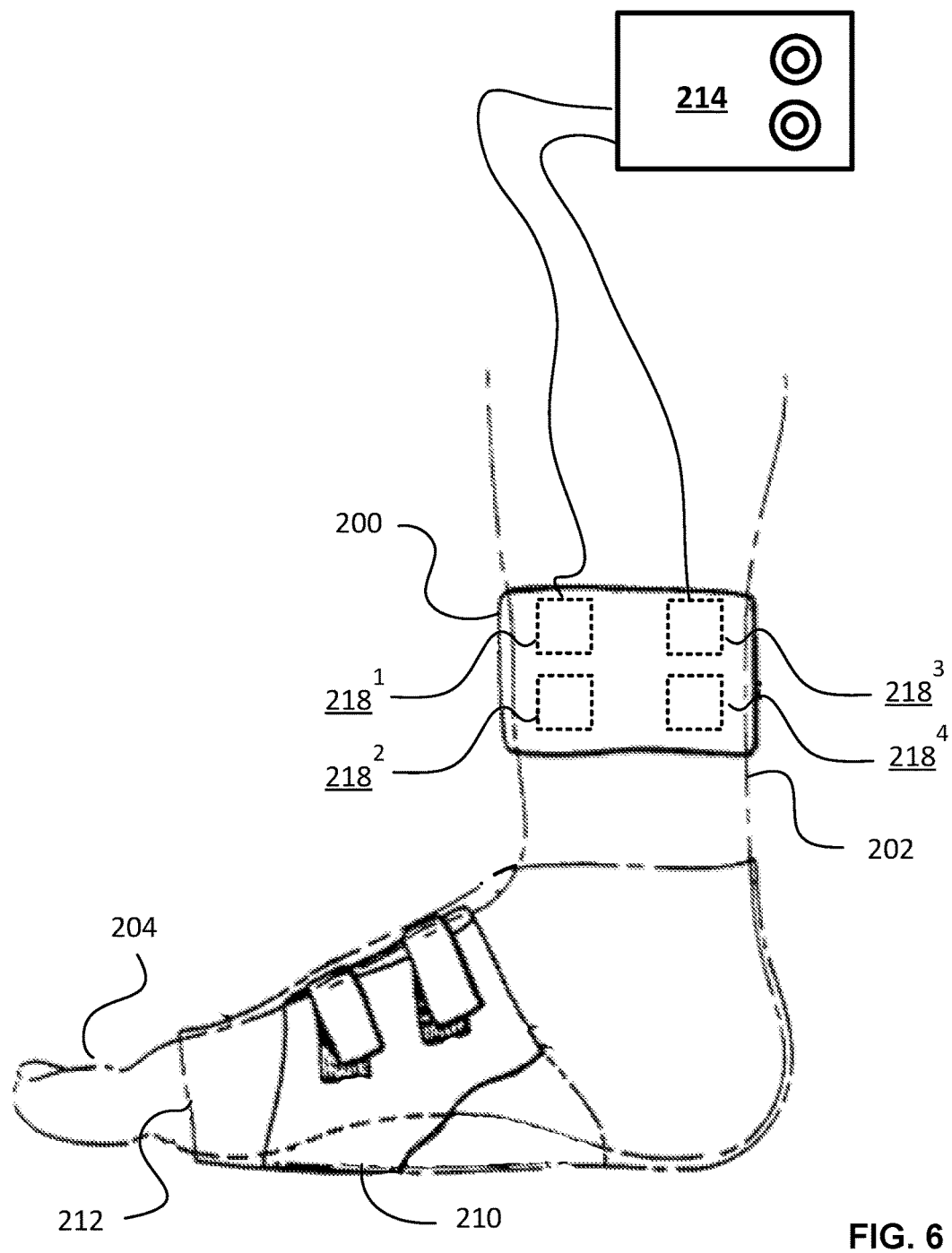
FIG. 6 is a perspective views of the cuff of FIGS. 4A-D being used on a patient's ankle.

Additionally, as noted above, in addition to promoting post-operative healing, there are other scenarios in which the invention may be used to stimulate vasodilation, and thereby increase blood flow. For example, as shown in FIG. 6, the present invention can be used for the treatment of peripheral vascular disease in the foot. In this case, the cuff (200) may be secured to the patient above the ankle (202). As a result, the electrode pairs ($218^1/218^2$), ($218^3/218^4$), receiving power from the power supply (214) as described above, deliver IFC therapy to increase blood flow to the patient's foot (204).

Optionally, the cuff (200) can be used in conjunction with a form of footwear, such as, for example, a wrap (210) covered by an open-toed slipper or bootie (212) configured to have a shape corresponding to the shape of a foot (204), and has the electrodes ($218''$) in the appropriate locations to provide their therapeutic effect. Such footwear coverings can include surgical foot drapes, wraps, disposable or reusable booties, Rooke® boots, and any other offloading or vascular boots that may be required when treating feet. As noted above, a user input may be provided that allows a user to set the Hz level to program the foot covering for either vasoconstriction or vasodilatation, depending on what is desired.

Similarly, the cuff (200) can be used to increase blood flow to the foot after debridement surgery for diabetic foot ulcers. By using the cuff (200) to apply IFC, vessels in borderline living tissue following the surgery can be stimulated to provide arterial perfusion.

Figure 7:
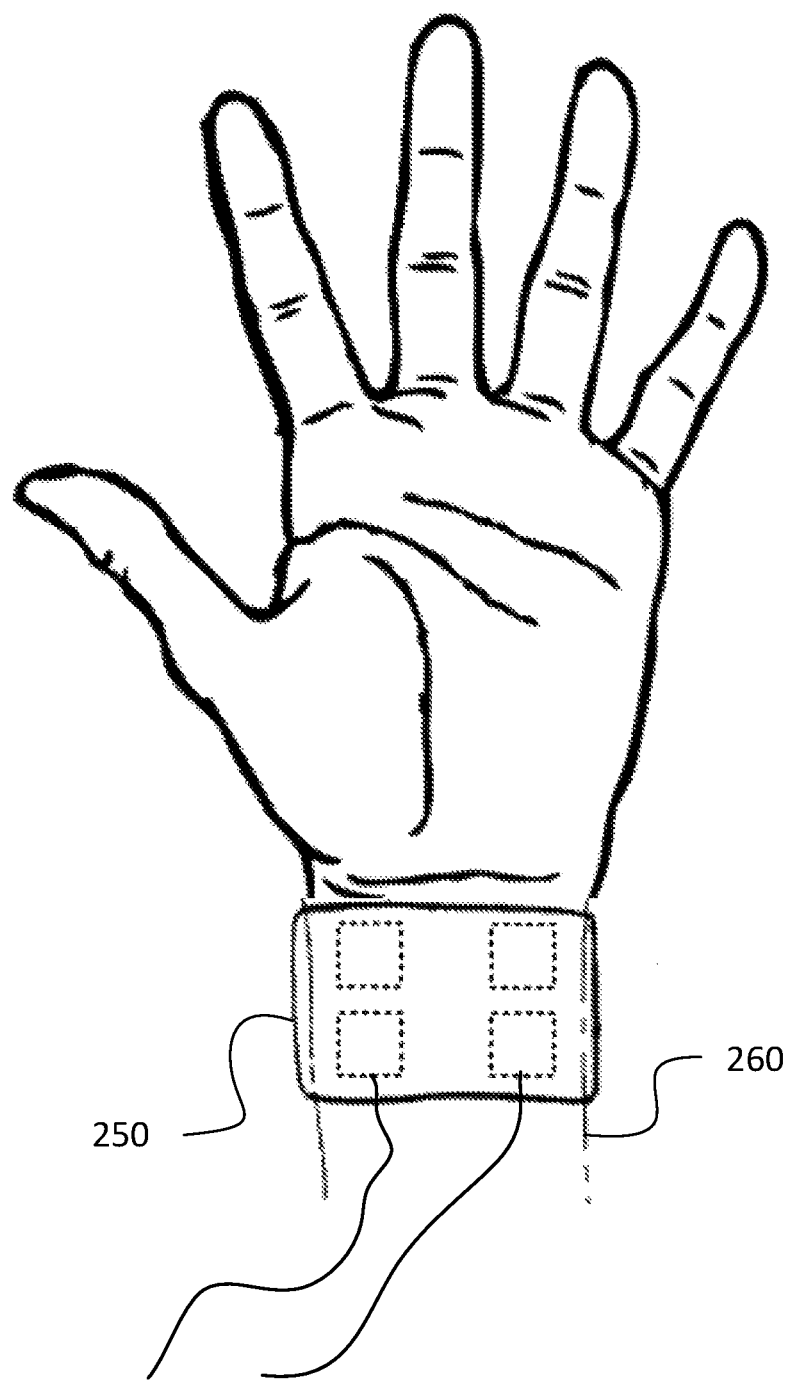
FIG. 7 is a perspective view of the cuff of FIGS. 4A-D being used on a patient's wrist.

Similarly, as shown in FIG. 7, a cuff (250) can be secured to a patient's wrist (260) to treat carpal tunnel syndrome. In this way, one is able to increase blood flow to the median nerve.

An additional potential synergistic outcome of using the above-described device employing electrical stimulation is a decrease in infection rates, which also has a further positive effective on healing.

Although the invention has been described with reference to particular arrangement of parts, features, and the like, these are not intended to exhaust all possible arrangements or features, and indeed many modifications and variations will be ascertainable by those of skill in the art.

The present invention is designed so that any electrical or mechanical types of deep penetration electrical stimulation that is non-invasive and external (i.e. transcutaneous) that are available but have not been incorporated into the description of the invention, or that become available as technology advances, are considered part of the invention and incorporated by modifying the electrical and mechanical parts and protocols associated with them to the achieve the aims of the present invention.

What is claimed is:

1. A device for controlling blood flow, comprising:
a cuff configured to mount to an extremity of a patient;
wherein the cuff includes a plurality of electrodes electrically connectable to an interferential current supply that supplies current to the plurality of electrodes; and
wherein the electrodes supply electrical impulses to the extremity of the patient in response to the current received from the interferential current supply, the plurality of electrodes comprising a first pair of electrodes supplying a first electrical impulse at a first frequency, and a second pair of electrodes supplying a second electrical impulse at a second frequency different from the first frequency;
wherein the first and second pairs of electrodes are positioned on the cuff such that the first and second electrical impulses intersect at a target area; and
wherein the interferential current supply simultaneously supplies current to the first and second pairs of electrodes such that the first and second electrical impulses give rise to at least one beat impulse having an interference frequency lower than the first and second frequencies at the target area.

2. The device of claim 1, wherein the first and second pairs of electrodes supply first and second impulses at first and second frequencies that give rise to a beat impulse that has a sympathetic nerve stimulation property to induce vasoconstriction of blood vessels.

3. The device of claim 1, wherein the first and second pairs of electrodes supply first and second impulses at first and second frequencies that give rise to a beat impulse that has a parasympathetic nerve stimulation property to induce vasodilatation of blood vessels.

4. The device of claim 1, wherein the cuff comprises an inflatable cuff.

5. The device of claim 1, further comprising a fluid source that supplies fluid to the inflatable cuff to provide pneumatic pressure.

6. The device of claim 1, wherein the cuff includes additional pairs of electrodes, each pair giving rise to at least one beat impulse having an interference frequency.

7. The device of claim 1, wherein the electrodes are embedded within the cuff.

8. The device of claim 1, wherein each electrode includes an adhesive on a surface thereof, with which the electrode is affixed to an outer surface of the cuff.

9. The device of claim 1, wherein:
the cuff includes a plurality of electrically conductive fabric segments of fabric; and
the electrodes comprise the electrically conductive fabric segments.

10. The device of claim 1, further comprising:
a controller;
the interferential current supply in communication with the controller;
a sensor providing sensor feedback to the controller, the sensor indicative of the state of blood flow at the extremity;
wherein the controller causes the interferential current supply to supply current to the plurality of electrodes based at least in part on the state of blood flow.

11. The device of claim 10, wherein the sensor comprises monitoring device.

12. The device of claim 10, wherein the sensor comprises a Doppler ultrasound probe.

13. The device of claim 1, wherein each electrode includes an electrical connector for connecting a wire to the interferential current supply.

14. The device of claim 1, wherein the electrodes include at least one antenna for receiving power wirelessly.

15. A device for controlling blood flow, comprising:
an interferential current supply;
a cuff configured to mount to an extremity of a patient, the cuff including at least first and second pairs of electrodes connected to the interferential current supply;
wherein, when the first and second pairs of electrodes supply electrical impulses to the extremity of the patient in response to current received from the interferential current supply, the first pair of electrodes supplying a first electrical impulse at a first frequency, and the second pair of electrodes supplying second electrical impulse at a second frequency different from the first frequency;
wherein the first and second pairs of electrodes are positioned on the cuff such that the first and second electrical impulses intersect at a target area; and
wherein the interferential current supply simultaneously supplies current to the first and second pairs of electrodes such that the first and second electrical impulses give rise to at least one beat impulse having an interference frequency lower than the first and second frequencies at the target area.

16. A method of controlling blood flow, the method comprising:
mounting a cuff to an extremity of a patient, the cuff having a plurality of electrodes;
connecting at least first and second pairs of electrodes to an interferential current supply;
supplying a first electrical impulse at a first frequency to a target area by supplying current to the first pair of electrodes from the interferential current supply;
supplying a second electrical impulse at a second frequency different from the first frequency to the target area, at the same time the first electrical impulse is supplied to the target area, by supplying current to the second pair of electrodes such that the second electrical impulse intersects with the first electrical impulse at the target area, the first and second electrical impulses giving rise to at least one beat impulse having an interference frequency lower than the first and second frequencies at the target area.

17. The method of claim 16, wherein the step of mounting a cuff to the extremity of a patient comprises mounting the cuff to the patient's ankle.

18. The method of claim 16, wherein the step of mounting a cuff to the extremity of a patient comprises mounting the cuff to the patient's wrist.

19. The method of claim 16, wherein the step of mounting a cuff to the extremity of a patient comprises mounting the cuff to the patient's thigh.

* * * * *